United States Patent
Kay et al.

(10) Patent No.: US 9,359,623 B2
(45) Date of Patent: Jun. 7, 2016

(54) METHODS AND COMPOSITIONS FOR THE PRODUCTION OF FATTY ACIDS IN PHOTOSYNTHETIC PROKARYOTIC MICROORGANISMS

(75) Inventors: Steve A. Kay, San Diego, CA (US); Ewa Lis, Lakeside, CA (US); Susan Golden, Del Mar, CA (US); Michael Melnick, San Francisco, CA (US); Dawn M. Adin, Germantown, MD (US); James W. Golden, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/383,409

(22) PCT Filed: Jul. 22, 2010

(86) PCT No.: PCT/US2010/042842
§ 371 (c)(1),
(2), (4) Date: Apr. 5, 2012

(87) PCT Pub. No.: WO2011/011568
PCT Pub. Date: Jan. 27, 2011

(65) Prior Publication Data
US 2012/0184004 A1 Jul. 19, 2012

Related U.S. Application Data

(60) Provisional application No. 61/228,411, filed on Jul. 24, 2009.

(51) Int. Cl.
*C12P 7/64* (2006.01)
*C12N 9/16* (2006.01)
*C12N 9/88* (2006.01)
*G01N 33/92* (2006.01)

(52) U.S. Cl.
CPC ............ *C12P 7/6409* (2013.01); *C12N 9/16* (2013.01); *C12N 9/88* (2013.01); *G01N 33/92* (2013.01); *Y02P 20/52* (2015.11)

(58) Field of Classification Search
CPC .......... C12P 7/64; C12N 1/20; C12N 9/0071; C12N 9/16; C12Y 114/19002; C12Y 301/02014
USPC ............................. 435/134, 252.3, 189, 196
See application file for complete search history.

(56) References Cited

U.S. PATENT DOCUMENTS

| 5,298,421 | A | 3/1994 | Davies et al. |
| 5,512,482 | A | 4/1996 | Voelker et al. |
| 5,667,997 | A | 9/1997 | Voelker et al. |
| 5,807,893 | A | 9/1998 | Voelker |
| 5,945,585 | A | 8/1999 | Hitz et al. |
| 2009/0087890 | A1 | 4/2009 | Pyle et al. |
| 2009/0170184 | A1* | 7/2009 | Shepherd et al. ............. 435/244 |
| 2009/0176272 | A1 | 7/2009 | Champagne et al. |
| 2009/0298143 | A1 | 12/2009 | Roessler et al. |
| 2010/0081177 | A1* | 4/2010 | Schatz et al. .................. 435/134 |
| 2010/0081178 | A1 | 4/2010 | Roberts et al. |
| 2010/0255551 | A1 | 10/2010 | Roberts et al. |
| 2010/0304432 | A1 | 12/2010 | O'Keefe et al. |
| 2010/0311157 | A1 | 12/2010 | Van Alstyne et al. |
| 2011/0020883 | A1 | 1/2011 | Roessler et al. |
| 2011/0053216 | A1 | 3/2011 | Vermaas |
| 2013/0143306 | A1 | 6/2013 | Berry et al. |

FOREIGN PATENT DOCUMENTS

| WO | 2007136762 A2 | 11/2007 |
| WO | WO 2008/119082 A2 * | 10/2008 |
| WO | WO 2008/147781 A2 * | 12/2008 |
| WO | WO 2009/076559 A1 * | 6/2009 |

OTHER PUBLICATIONS

Nishida et al., Ann. Rev. Plant Physiol. Plant Mol. Biol. 47:541-568, 1996.*
Oleic Acid, Jun. 1999, obtained from cameochemicals.noaa.gov/chris/OLA.pdf, 2 pages.*
Hitz et al., Plant Physiol. 105:635-641, 1994.*
Cahoon et al., J. Bacteriol. 178:936-939, 1996.*
Voelker et al., "Alteration of the Specificity and Regulation of Fatty Acid Synthesis of *Escherichia coli* by Expression of a Plant Medium-Chain Acyl-Acyl Carrier Protein Thioesterase", Journal of Bacteriology, Dec. 1994, pp. 7320-7327, vol. 176, No. 23.
Dehesh et al., "Production of high levels of 8:0 and 10:0 fatty acids in transgenic canola by overexpression of Ch FatB2, a thioesterase of cDNA from Cuphea hookeriana", The Plant Journal (1996) 9(2), 167-172.
Voelker et al., "Broad-Range and Binary-Range Acyl-Acyl-Carrier-Protein Thioesterases Suggest an Alternative Mechanism for Medium-Chain Production in Seeds", Plant Physiol. (1997) 114:669-677.
Kim, Yun-Kyung, International Search Report and Written Opinion, PCT/US2010/042842, Korean Intellectual Property Office, Apr. 12, 2011.
Nickitas-Etienne, Athina, International Preliminary Report on Patentability, PCT/US2010/042842, The International Bureau of WIPO, Jan. 24, 2012.

(Continued)

*Primary Examiner* — David J Steadman
(74) *Attorney, Agent, or Firm* — Gregory P. Einhorn; Greer Burns & Crain LLP

(57) ABSTRACT

Provided herein are methods and compositions for the production of renewable fatty acids from photosynthetic prokaryotic microorganisms, such as a blue green algae, any specie of the phylum Cyanophyta, a chloroplast of a green algae and/or a Cyanobacterium. Engineered or natural strains of these organisms or organelles can be used to produce both saturated and unsaturated fatty acids with variable chain length specificity from 8-18 carbons. The fatty acids can then be secreted into the culture medium, allowing for rapid, continuous and efficient separation of fatty acid product without harvesting of cell mass.

19 Claims, 4 Drawing Sheets

(56) References Cited

OTHER PUBLICATIONS

Alonso, et al. (1995) Plant Mol. Biol. 29:1211-1221.
Mazouni, et al. (2003) Mol. Microbiol. Aug;49(4):1019-29.
Nagai & Bloch Apr. 25, 1966, JBC 241, 1925-1927.
Nagai & Bloch Sep. 10, 1968, JBC, 243, 4626-4633.
Schultz et al. Plant Physiology Oct. 2000 vol. 124 No. 2 681-692.
Yee, et al., Archives of Microbiology, Sep. 1981, vol. 130, Issue 1, pp. 14-18.

* cited by examiner

METHODS AND COMPOSITIONS FOR THE PRODUCTION OF FATTY ACIDS IN PHOTOSYNTHETIC PROKARYOTIC MICROORGANISMS

CROSS-REFERENCE TO RELATED APPLICATIONS

This United States Utility patent application is the §371 national phase of PCT international patent application No. PCT/US2010/042842, having an international filing date of Jul. 22, 2010, which claims benefit of priority to U.S. Provisional Patent Application Ser. Nos. (USSN) 61/228,411, filed Jul. 24, 2009. The aforementioned applications are expressly incorporated herein by reference in their entirety and for all purposes.

FIELD OF THE INVENTION

The invention generally related to alternative energy production, biofuels, microbiology and molecular biology. In alternative embodiments, the invention provides methods and compositions for the production of fatty acids in photosynthetic prokaryotic microorganisms such as blue green algae, any specie of the phylum Cyanophyta and/or a Cyanobacterium, including e.g., Anabaena and Synechococcus.

BACKGROUND

Currently, renewable fatty acids are obtained solely from plant oils. Medium chain fatty acids (C8-C14) are typically sourced from coconut and palm oil, whereas longer chain saturated and unsaturated fatty acids are typically sourced from tallow, soy, corn or sunflower oil. Fatty acids are widely used for food, personal care products, industrial applications (e.g., lubricants, adhesives, detergents and plastics), as well as increasingly as biofuels. The demand for renewable fatty acids is rising and expanding.

With the current understanding of biological pathways it becomes possible to utilize other organisms, especially microorganisms, for the production of renewable chemicals such as fatty acids. Microbial fatty acid synthesis proceeds via a stepwise addition of 2 carbon units onto a growing acyl chain bound to acyl carrier protein (ACP). The process begins as a condensation of acetyl-ACP and malonyl-ACP into acetoacetyl-ACP liberating $CO_2$ which drives the reaction forward. The second step involves reduction of acetoacetyl-ACP to D-3-hydroxybutyryl-ACP using NADPH. Following a dehydration to crotonyl-ACP and another reduction using NADPH, butyryl-ACP is formed. The chain elongation typically continues with further addition of malonyl-ACP until a C16 acyl chain is formed, which is then hydrolyzed by a thioesterase into a free C16 fatty acid.

Although many organisms show preference for fatty acid termination at C16 carbon chain length, various plant thioesterases show a broad range of specificity terminating at both shorter and longer chain lengths. Moreover, some thioesterases are capable of terminating monounsaturated fatty acids such as C16:1 (C16 refers to fatty acid with a 16 carbon chain and 1 refers to one double bond) and C18:1. For example, it has been shown previously that expression of medium chain plant thioesterases like FatB from *Umbellularia californica* in *E. coli* results in accumulation of high levels of medium chain fatty acids, primarily laurate (C12:0). Similarly, expression of *Cuphea palustris* FatB1 thioesterase in *E. coli* led to accumulation of C8-10:0 acyl-ACPs. Similarly, *Carthamus tinctorius* thioesterase, when expressed in *E. coli* leads to >50 fold elevation in C18:1 chain termination and release as free fatty acid. The accumulation of fatty acids has been shown to require preventing fatty acid β-oxidation. Mutation of the rate-limiting enzyme governing β-oxidation, acyl-CoA synthase, in *E. coli* has been shown to greatly improve the production of medium chain fatty acids.

Although the studies described above demonstrated that various fatty acids could be produced in *E. coli*, there are several disadvantages in using *E. coli* as opposed to using photosynthetic microorganisms as a production host for fatty acids. First of all, production of any renewable chemical in *E. coli* requires high cost fermentation using sugar which itself has to come from plant sources. In contrast, photosynthetic microorganisms directly utilize carbon dioxide and sunlight as an energy source and in the case of cyanobacteria, many also utilize atmospheric nitrogen gas as a nitrogen source. There are also several differences in *E. coli* metabolism that differentiate it from the photosynthetic microorganisms such as cyanobacteria with respect to biosynthesis and utilization of fatty acids. Whereas *E. coli* requires inactivation of the fatty acid β-oxidation pathway to allow for any significant production of fatty acids, similar measures are not generally required in Cyanobacteria, which appear not to utilize fatty acids as an energy source—thus allowing for high levels of their production. This likely stems not only from the fact that cyanobacteria are generally photoautotrophs (unlike *E. coli*, which are heterotrophs), but also stem from the profound difference in utilization of exogenous fatty acids by the two organisms. *E. coli* utilizes exogenous fatty acids as an energy source by coupling them to CoA with the help of acyl-CoA synthetase. The acyl-CoA precursors are then broken down to acetyl-CoA. Cyanobacteria lack this activity; instead, they couple exogenous fatty acids to ACP using acyl-ACP synthase. Those precursors are then gradually incorporated into lipids. Thus, whereas acyl-CoA synthetase activity in *E. coli* directly competes with a thioesterase by committing the acyl chain to a degradation pathway, the acyl-ACP synthetase in Cyanobacteria simply reverses the thioesterase activity.

In addition to changes in fatty acid utilization, Cyanobacteria biosynthesize only saturated fatty acids (C16:0 and C18:0) as opposed to *E. coli*, which biosynthesizes both saturated and unsaturated fatty acids. Thus expression solely of a thioesterase in Cyanobacteria results in production of only saturated fatty acids—a more pure feedstock as opposed to a mixture of saturated and unsaturated fatty acids produced by *E. coli*. To generate unsaturated fatty acids in cyanobacteria, an ACP-desaturase and a thioesterase may be co-expressed. Whereas ACP-desaturases are inactive in *E. coli* due to lack of ferredoxin, cyanobacteria do not have that limitation.

SUMMARY

In alternative embodiments, the invention provides methods and compositions for the production of fatty acids in photosynthetic prokaryotic microorganisms, including any blue green algae, any specie of the phylum Cyanophyta and/or Cyanobacterium, including e.g., Anabaena and Synechococcus.

In alternative embodiments, the invention provides for producing a fatty acid in a photosynthetic prokaryotic microorganism, comprising: introducing a nucleic acid comprising a promoter sequence operably linked to a heterologous nucleic acid sequence encoding a polypeptide which produces (or catalyzes the synthesis of) a fatty acid into (or in) a photosynthetic prokaryotic microorganism; and culturing the photosynthetic prokaryotic microorganism, thereby producing the fatty acid, wherein optionally the fatty acid comprises a renewable fatty acid.

In alternative embodiments of the methods the promoter sequence comprises an inducible promoter sequence or a constitutive promoter sequence; or, the heterologous nucleic acid sequence comprises an endogenous nucleic acid sequence or an exogenous nucleic acid sequence. The heterologous nucleic acid sequence can encode an enzyme, or a polypeptide having enzymatic activity.

In alternative embodiments, the enzyme comprises a thioesterase or an esterase; and/or a β-hydroxydecanoyl dehydrase. The thioesterase can comprise an acyl-ACP thioesterase, an oleoyl-ACP thioesterase and/or a palmitoleoyl-ACP thioesterase.

In alternative embodiments, a signaling sequence, or an N-terminal plastid signaling sequence, has been removed from the enzyme or polypeptide.

In alternative embodiments, the nucleic acid comprises a plurality of nucleic acid sequences encoding a plurality of enzymes, and/or a plurality of thioesterases or esterases; and/or a β-hydroxydecanoyl dehydrase.

In alternative embodiments, the heterologous nucleic acid sequence encodes an ACP-desaturase, or, the ACP-desaturase comprises a stearoyl-ACP-desaturase. The nucleic acid can comprise a plurality of nucleic acid sequences which encode at least one thioesterase and at least one ACP-desaturase; or co-express an oleoyl-ACP thioesterase and a stearoyl-ACP desaturase. In alternative embodiments, the plurality of nucleic acid sequences further comprises a nucleic acid sequence encoding an oleoyl-ACP thioesterase.

In alternative embodiments, the nucleic acid further comprises a sequence selected from the group consisting of: a lacI repressor binding site, a Ptrc promoter, a lac operon, a gene of interest, an rrnB terminator sequence, an antibiotic resistance marker, and an origin of replication.

In alternative embodiments, the photosynthetic prokaryotic microorganism is a blue green algae, any specie of the phylum Cyanophyta, a chloroplast or derivative thereof of a green algae, a Cyanobacterium. The Cyanobacterium can be selected from the group consisting of: *Anabaena* sp., *Aphanizomenon* sp., *Aphanocapsa* sp., *Aphanothece* sp., *Arthrospira* sp., *Calothrix* sp., *Cylindrospermum* sp., *Dermocarpa* sp., *Eucapsis* sp., *Fischerella* sp., *Geitlerinema* sp., *Gloeocapsa* sp., *Gloeotrichia* sp., *Lyngbya* sp., *Mastigocladus* sp., *Merismopedia* sp., *Microcoleus* sp., *Microcystis* sp., *Nodularia* sp., *Nostoc* sp., *Oscillatoria* sp., *Phormidium* sp., *Plectonema* sp., *Pseudoanabaena* sp., *Schizotrix* sp., *Scytonema* sp., *Spirulina* sp., *Starria* sp., *Symphyonemopsis* sp., *Symploca* sp., *Synechococcus* sp., *Synechocystis* sp. and *Tolypothrix* sp. The Cyanobacterium can be selected from the group consisting of: *Anabaena* sp., *Nostoc* sp. and *Nodularia* sp. The Cyanobacterium can be selected from the group consisting of: *Synechococcus* sp., *Synechocystis* sp. and *Aphanothece* sp. The Cyanobacterium can be selected from the group consisting of: *Lyngbya* sp., *Oscillatoria* sp., *Phormidium* sp., *Pseudoanabaena* sp., *Arthrospira* sp. and *Spirulina* sp.

In alternative embodiments, the fatty acid is saturated or unsaturated, or the produced fatty acid comprises a saturated fatty acid, an unsaturated fatty acid or a combination thereof. The fatty acid can have a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

In alternative embodiments, methods of the invention further comprise extracting the fatty acid from the photosynthetic prokaryotic microorganism and/or culture medium. The extraction can comprise extraction from a culture medium, an aqueous media or an aqueous culture media, or the extraction can comprise a solid phase extraction. In alternative embodiments, the extraction comprises skimming the surface of a culture comprising the photosynthetic prokaryotic microorganism.

In alternative embodiments, methods of the invention further comprise analyzing (analysis of) the fatty acid, and/or quantifying the amount of fatty acid produced. The analysis can be performed using (the analysis comprises using) one or more HP-FFAP™ (Agilent, Santa Clara, Calif., US) columns coupled to a gas chromatography mass spectrometry.

In alternative embodiments, the invention provides methods for producing a fatty acid in a photosynthetic prokaryotic microorganism, comprising: contacting a photosynthetic prokaryotic microorganism with a compound capable of inducing production of a fatty acid in the microorganism; and culturing the photosynthetic prokaryotic microorganism, thereby producing the fatty acid, wherein optionally the fatty acid comprises a renewable fatty acid, wherein optionally the fatty acid is saturated or unsaturated, or the produced fatty acid comprises a saturated fatty acid, an unsaturated fatty acid or a combination thereof, wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons, wherein optionally the photosynthetic prokaryotic microorganism is a blue green algae, any specie of the phylum Cyanophyta, a chloroplast or derivative thereof of a green algae, a Cyanobacterium.

In alternative embodiments of the methods, the compound capable of inducing production of the fatty acid in the microorganism comprises a polypeptide, a nucleic acid, a lipid, an enzyme or a chemical or a combination thereof, and optionally the nucleic acid encodes at least one or a plurality of enzymes, and/or at least one or a plurality of thioesterases or esterases; and/or a β-hydroxydecanoyl dehydrase; or comprises co-expression of an oleoyl-ACP thioesterase and a stearoyl-ACP desaturase.

In alternative embodiments, the invention provides methods of screening a photosynthetic prokaryotic microorganism library for fatty acid secretion, comprising: collecting culture medium which is in contact with a photosynthetic prokaryotic microorganism, or collecting all or part of the culture medium of the photosynthetic prokaryotic microorganism; and determining whether the culture medium comprises a fatty acid or a renewable fatty acid, and optionally analyzing (analysis of) the fatty acid, and/or quantifying the amount of fatty acid produced, wherein optionally the fatty acid is saturated or unsaturated, or the produced fatty acid comprises a saturated fatty acid, an unsaturated fatty acid or a combination thereof, wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons, wherein optionally the photosynthetic prokaryotic microorganism is a blue green algae, any specie of the phylum Cyanophyta, a chloroplast or derivative thereof of a green algae, a Cyanobacterium.

In alternative embodiments, the invention provides isolated, synthetic or recombinant nucleic acids comprising (a) a promoter sequence operably linked to a heterologous nucleic acid sequence capable of producing a fatty acid or a renewable fatty acid, and (b) a sequence designed for (enabling the capability of) targeted integration of the nucleic acid in a photosynthetic prokaryotic microorganism, wherein optionally the integration comprises integration into a genome of the photosynthetic prokaryotic microorganism, or stable integration into a genome of the photosynthetic prokaryotic microorganism, and optionally the sequence designed for (enabling the capability of) targeted integration of the nucleic acid in the photosynthetic prokaryotic microorganism is fully or partially complementary to genomic sequence in the photosynthetic prokaryotic microorganism, and optionally the sequence is fully or partially complementary to a genome sequence of a blue green algae, any specie of the phylum Cyanophyta, a chloroplast of a green algae and/or a Cyanobacterium genome sequence, wherein optionally the fatty acid is saturated or unsaturated, or the produced fatty acid comprises a saturated fatty acid, an unsaturated fatty acid or a combination thereof, wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

The heterologous nucleic acid sequences can encode an enzyme or a polypeptide having enzymatic activity, or a plant enzyme or a polypeptide. The enzyme can comprise an esterase or a thioesterase (or a polypeptide having an esterase or a thioesterase activity); and/or a β-hydroxydecanoyl dehydrase. The thioesterase (or a polypeptide having thioesterase activity) can comprise an acyl-ACP thioesterase, an oleoyl-ACP thioesterase, a palmitoleoyl-ACP thioesterase or a combination thereof; or co-expression of an oleoyl-ACP thioesterase and a stearoyl-ACP desaturase.

In alternative embodiments, a signaling sequence, or an N-terminal plastid signaling sequence, has been removed from the enzyme or polypeptide.

In alternative embodiments, the nucleic acid comprises a plurality of heterologous nucleic acid sequences capable of producing a fatty acid or a renewable fatty acid, or a plurality of nucleic acid sequences encoding an enzyme, an esterase or a thioesterase or a combination thereof. In alternative embodiments, the heterologous nucleic acid sequence encodes a stearoyl-ACP-desaturase. In alternative embodiments, the heterologous nucleic acid sequence encodes an oleoyl-ACP thioesterase, or the nucleic acid further comprises a nucleic acid sequence encoding an oleoyl-ACP thioesterase.

In alternative embodiments, the nucleic acid further comprises a sequence selected from the group consisting of: a lacI repressor binding site, a Ptrc promoter, a lac operon, a gene of interest, an rrnB terminator sequence, an antibiotic resistance marker, and an origin of replication.

In alternative embodiments, the invention provides genetically modified photosynthetic prokaryotic microorganisms: (a) into which a heterologous nucleic acid encoding a polypeptide which produces a renewable fatty acid has been introduced; or, (b) into which the nucleic acid as provided herein has been introduced, wherein optionally the heterologous nucleic acid is transiently or stably introduced into the photosynthetic prokaryotic microorganism, or the heterologous nucleic acid is integrated into the genome of the photosynthetic prokaryotic microorganism, or is an episomal heterologous nucleic acid, wherein optionally the fatty acid is saturated or unsaturated, or the produced fatty acid comprises a saturated fatty acid, an unsaturated fatty acid or a combination thereof, wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

In alternative embodiments of the genetically modified microorganisms, the introduced nucleic acid comprises an endogenous nucleic acid or an exogenous nucleic acid. The nucleic acid can encode a polypeptide, an enzyme, an esterase or a thioesterase; or a plant polypeptide, enzyme, esterase or thioesterase; and/or a β-hydroxydecanoyl dehydrase. The thioesterase can be an acyl-ACP thioesterase, an oleoyl-ACP thioesterase and/or a palmitoleoyl-ACP thioesterase.

In alternative embodiments of the genetically modified microorganisms, a signaling sequence, or an N-terminal plastid signaling sequence, has been removed from the polypeptide, enzyme, esterase or thioesterase. In alternative embodiments, the nucleic acid comprises a plurality of nucleic acid sequences which encode a polypeptide, enzyme, esterase or thioesterase, and optionally the esterase or thioesterase comprises an oleoyl-ACP thioesterase. The nucleic acid can encode an ACP-desaturase, or the heterologous nucleic acid comprises or further comprises an ACP-desaturase. The ACP-desaturase can be a stearoyl-ACP-desaturase. The nucleic acid can comprise a plurality of nucleic acid sequences which encode a thioesterase and an ACP-desaturase. In alternative embodiments, the nucleic acid further comprises a nucleic acid sequence encoding an oleoyl-ACP thioesterase.

In alternative embodiments, the nucleic acid further comprises a sequence selected from the group consisting of: a lacI repressor binding site, a Ptrc promoter, a lac operon, a gene of interest, an rrnB terminator sequence, an antibiotic resistance marker, and an origin of replication.

In alternative embodiments, the genetically modified photosynthetic prokaryotic microorganism is (or comprises, or consists of) a blue green algae, any specie of the phylum Cyanophyta, a chloroplast or derivative thereof of a green algae and/or a Cyanobacterium.

In alternative embodiments, the invention provides genetically modified blue green algaes, a specie of the phylum Cyanophyta, or a Cyanobacterium, of any combination thereof, for the production of a renewable fatty acid, wherein (a) the genome of the genetically modified blue green algae, specie of the phylum Cyanophyta, or Cyanobacterium has integrated (transiently or stably) the nucleic acid as provided herein; or (b) the genetically modified blue green algae, specie of the phylum Cyanophyta, or Cyanobacterium comprises, or has contained within, a heterologous nucleic acid comprising a nucleic acid of the invention, wherein optionally the heterologous nucleic acid is transiently or stably introduced into the genetically modified blue green algae, specie of the phylum Cyanophyta, or Cyanobacterium, or the heterologous nucleic acid is integrated into the genome of the genetically modified blue green algae, specie of the phylum Cyanophyta, or Cyanobacterium, or is an episomal heterologous nucleic acid, wherein optionally the fatty acid is saturated or unsaturated, or the produced fatty acid comprises a saturated fatty acid, an unsaturated fatty acid or a combination thereof.

wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

In alternative embodiments, the invention provides genetically modified chloroplasts of a green algae modified for the production of a renewable fatty acid, wherein the genetically modified chloroplast comprises or has integrated (transiently or stably) a nucleic acid of the invention, wherein optionally the fatty acid is saturated or unsaturated, or the produced fatty acid comprises a saturated fatty acid, an unsaturated fatty acid or a combination thereof.

wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

In alternative embodiments, the invention provides artificial or synthetic cells or artificial or synthetic organelles comprising a genetically modified chloroplast of a green algae modified for the production of a renewable fatty acid, wherein the artificial cell or organelle comprises or has integrated (transiently or stably) a nucleic acid of the invention, wherein optionally the fatty acid is saturated or unsaturated, or the produced fatty acid comprises a saturated fatty acid, an unsaturated fatty acid or a combination thereof.

wherein optionally the fatty acid has a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

Expression of the plant thioesterases in Cyanobacteria resulted in high levels of secretable fatty acids; this was obtained following modification of the plant thioesterase genes. Specifically, removal of the N-terminal plastid signaling sequences significantly improved yield of fatty acids obtained as shown below.

Due to propensity of Cyanobacteria to undergo homologous recombination, the engineered Cyanobacteria strains of the invention are inherently more stable than *E. coli* strains, which carry plasmids and are susceptible to loss of those plasmids and subsequently loss of thioesterase activity due to toxicity of expression of the thioesterases.

In one embodiment, a method for producing a renewable fatty acid in a photosynthetic prokaryotic microorganism is provided, comprising: introducing a nucleic acid comprising a promoter sequence operably linked to a heterologous nucleic acid sequence encoding a polypeptide which produces a renewable fatty acid into a photosynthetic prokaryotic microorganism; and culturing the photosynthetic prokaryotic microorganism, thereby producing the renewable fatty acid. In one aspect of this embodiment, the promoter sequence is an inducible promoter sequence. In another aspect of this embodiment, the heterologous nucleic acid sequence is endogenous. In a further aspect of this embodiment, the heterologous nucleic acid sequence is exogenous. In a further aspect of this embodiment, the heterologous nucleic acid sequence encodes a thioesterase. In a further aspect of this embodiment, the thioesterase is an acyl-ACP thioesterase. In a further aspect of this embodiment, the thioesterase is an oleoyl-ACP thioesterase. In a further aspect of this embodiment, the thioesterase is a palmitoleoyl-ACP thioesterase. In a further aspect of this embodiment, an N-terminal plastic signaling sequence has been removed from the thioesterase. In a further aspect of this embodiment, the nucleic acid comprises a plurality of nucleic acid sequences which encode a thioesterase. In a further aspect of this embodiment, the heterologous nucleic acid sequence encodes an ACP-desaturase. In a further aspect of this embodiment, the ACP-desaturase is a stearoyl-ACP-desaturase. In a further aspect of this embodiment, the nucleic acid comprises a plurality of nucleic acid sequences which encode a thioesterase and an ACP-desaturase. In a further aspect of this embodiment, the nucleic acid further comprises a nucleic acid sequence which encodes an oleoyl-ACP thioesterase. In a further aspect of this embodiment, the nucleic acid further comprises a sequence selected from the group consisting of: a lacI repressor binding site, a Ptrc promoter, a lac operon, a gene of interest, an rrnB terminator sequence, an antibiotic resistance marker, and an origin of replication.

In a further aspect of this embodiment, the photosynthetic prokaryotic microorganism is any specie from the phylum Cyanobacterium, including any member of the class Chroobacteria, Hormogoneae and/or Gloeobacteria; or any member of the order Chroococcales, Gloeobacterales, Nostocales, Oscillatoriales, Pleurocapsales and/or Stigonematales; or any member of the family Prochloraceae and/or Prochlorotrichaceae; or any member of the genera *Halospirulina, Planktothricoides, Prochlorococcus, Prochloron* and/or *Prochlorothrix*. In a further aspect of this embodiment, the Cyanobacterium, is selected from the group consisting of: *Anabaena* sp., *Aphanizomenon* sp., *Aphanocapsa* sp., *Aphanothece* sp., *Arthrospira* sp., *Calothrix* sp., *Cylindrospermum* sp., *Dermocarpa* sp., *Eucapsis* sp., *Fischerella* sp., *Geitlerinema* sp., *Gloeocapsa* sp., *Gloeotrichia* sp., *Lyngbya* sp., *Mastigocladus* sp., *Merismopedia* sp., *Microcoleus* sp., *Microcystis* sp., *Nodularia* sp., *Nostoc* sp., *Oscillatoria* sp., *Phormidium* sp., *Plectonema* sp., *Pseudoanabaena* sp., *Schizotrix* sp., *Scytonema* sp., *Spirulina* sp., *Starria* sp., *Symphyonemopsis* sp., *Symploca* sp., *Synechococcus* sp., *Synechocystis* sp. and *Tolypothrix* sp. In a further aspect of this embodiment, the Cyanobacterium is selected from the group consisting of: *Anabaena* sp., *Nostoc* sp. and *Nodularia* sp. In an alternative embodiment, the Cyanobacterium is selected from the group consisting of: *Synechococcus* sp., *Synechocystis* sp. and *Aphanothece* sp. In a further aspect of this embodiment, the Cyanobacterium is selected from the group consisting of: *Lyngbya* sp., *Oscillatoria* sp., *Phormidium* sp., *Pseudoanabaena* sp., *Arthrospira* sp. and *Spirulina* sp.

In alternative embodiments, the fatty acids produced using methods or compositions of the invention are saturated, or unsaturated, or a combination thereof. In a further aspect of this embodiment, the fatty acid is has a variable chain length specificity of about 8 to about 18 carbons, or between about 6 to about 20 carbons, or about 6, 7, 8, 9, 10, 11, 12, 13, 14, 15, 16, 17, 18, 19 or 20 or more carbons.

In a further aspect of this embodiment, the method further comprises extracting the renewable fatty acid from the photosynthetic prokaryotic microorganism. In a further aspect of this embodiment, the extraction comprises extraction from an aqueous media. In a further aspect of this embodiment, the extraction comprises a solid phase extraction. In a further aspect of this embodiment, the extraction comprises skimming the surface of a culture comprising the photosynthetic prokaryotic microorganism. In a further aspect of this embodiment, the method further comprises analyzing the renewable fatty acid. In a further aspect of this embodiment, the analysis is performed using HP-FFAP™ (Agilent, Santa Clara, Calif., US) columns coupled to gas chromatography mass spectrometry.

In another embodiment, a method for producing a renewable fatty acid in a photosynthetic prokaryotic microorganism is provided, comprising: contacting a photosynthetic prokaryotic microorganism with a compound capable of inducing production of a renewable fatty acid in the microorganism; and culturing the photosynthetic prokaryotic microorganism, thereby producing the renewable fatty acid. In one aspect of this embodiment, the compound is an enzyme. In another aspect of this embodiment, the compound is a chemical.

Another embodiment is a method of screening a photosynthetic prokaryotic microorganism library for fatty acid secretion, comprising: collecting culture medium which is in contact with a photosynthetic prokaryotic microorganism; and determining whether the culture medium comprises a renewable fatty acid.

In a further embodiment, a nucleic acid for targeted integration in a photosynthetic prokaryotic microorganism is provided, comprising a promoter sequence operably linked to a heterologous nucleic acid sequence capable of producing a renewable fatty acid. In one aspect of this embodiment, the heterologous nucleic acid sequence encodes a thioesterase. In another aspect of this embodiment, the thioesterase is an acyl-ACP thioesterase. In a further aspect of this embodiment, the thioesterase is an oleoyl-ACP thioesterase. In a further aspect of this embodiment, the thioesterase is a palmitoleoyl-ACP thioesterase. In a further aspect of this embodiment, an N-terminal plastic signaling sequence has been removed from the thioesterase.

In a further aspect of this embodiment, the nucleic acid comprises a plurality of nucleic acid sequences which encode a thioesterase. In a further aspect of this embodiment, the heterologous nucleic acid sequence encodes a stearoyl-ACP-desaturase. In a further aspect of this embodiment, the nucleic acid further comprises a nucleic acid sequence which encodes an oleoyl-ACP thioesterase. In a further aspect of this embodiment, the nucleic acid further comprises a sequence selected from the group consisting of: a lacI repressor binding site, a Ptrc promoter, a lac operon, a gene of interest, an rrnB terminator sequence, an antibiotic resistance marker, and an origin of replication.

In a further embodiment, a genetically modified photosynthetic prokaryotic microorganism is provided into which a nucleic acid encoding a polypeptide which produces a renewable fatty acid has been introduced. In one aspect of this embodiment, the nucleic acid is endogenous. In another aspect of this embodiment, the nucleic acid is exogenous. In a further aspect of this embodiment, the nucleic acid encodes a thioesterase. In a further aspect of this embodiment, the thioesterase is an acyl-ACP thioesterase. In a further aspect of this embodiment, the thioesterase is an oleoyl-ACP thioesterase. In a further aspect of this embodiment, the thioesterase is a palmitoleoyl-ACP thioesterase. In a further aspect of this embodiment, an N-terminal plastic signaling sequence has been removed from the thioesterase. In a further aspect of this embodiment, the nucleic acid comprises a plurality of nucleic acid sequences which encode a thioesterase. In a further aspect of this embodiment, the nucleic acid encodes an ACP-desaturase. In a further aspect of this embodiment, the ACP-desaturase is a stearoyl-ACP-desaturase. In a further aspect of this embodiment, the nucleic acid comprises a plurality of nucleic acid sequences which encode a thioesterase and an ACP-desaturase. In a further aspect of this embodiment, the nucleic acid further comprises a nucleic acid sequence which encodes an oleoyl-ACP thioesterase. In a further aspect of this embodiment, the nucleic acid further comprises a sequence selected from the group consisting of: a lacI repressor binding site, a Ptrc promoter, a lac operon, a gene of interest, an rrnB terminator sequence, an antibiotic resistance marker, and an origin of replication.

In a further embodiment, a genetically modified cyanobacterium for the production of a renewable fatty acid is provided, where the genome of the genetically modified cyanobacterium has integrated a nucleic acid for targeted integration in a photosynthetic prokaryotic microorganism, where the nucleic acid comprises a promoter sequence operably linked to a heterologous nucleic acid sequence capable of producing a renewable fatty acid.

The details of one or more embodiments of the invention are set forth in the description below. Other features, objects, and advantages of the invention will be apparent from the description and from the claims.

All publications, patents, patent applications, GenBank sequences and ATCC deposits, cited herein are hereby expressly incorporated by reference for all purposes.

BRIEF DESCRIPTION OF THE DRAWINGS

Like reference symbols in the various drawings indicate like elements.

DETAILED DESCRIPTION OF THE INVENTION

Figure 1:
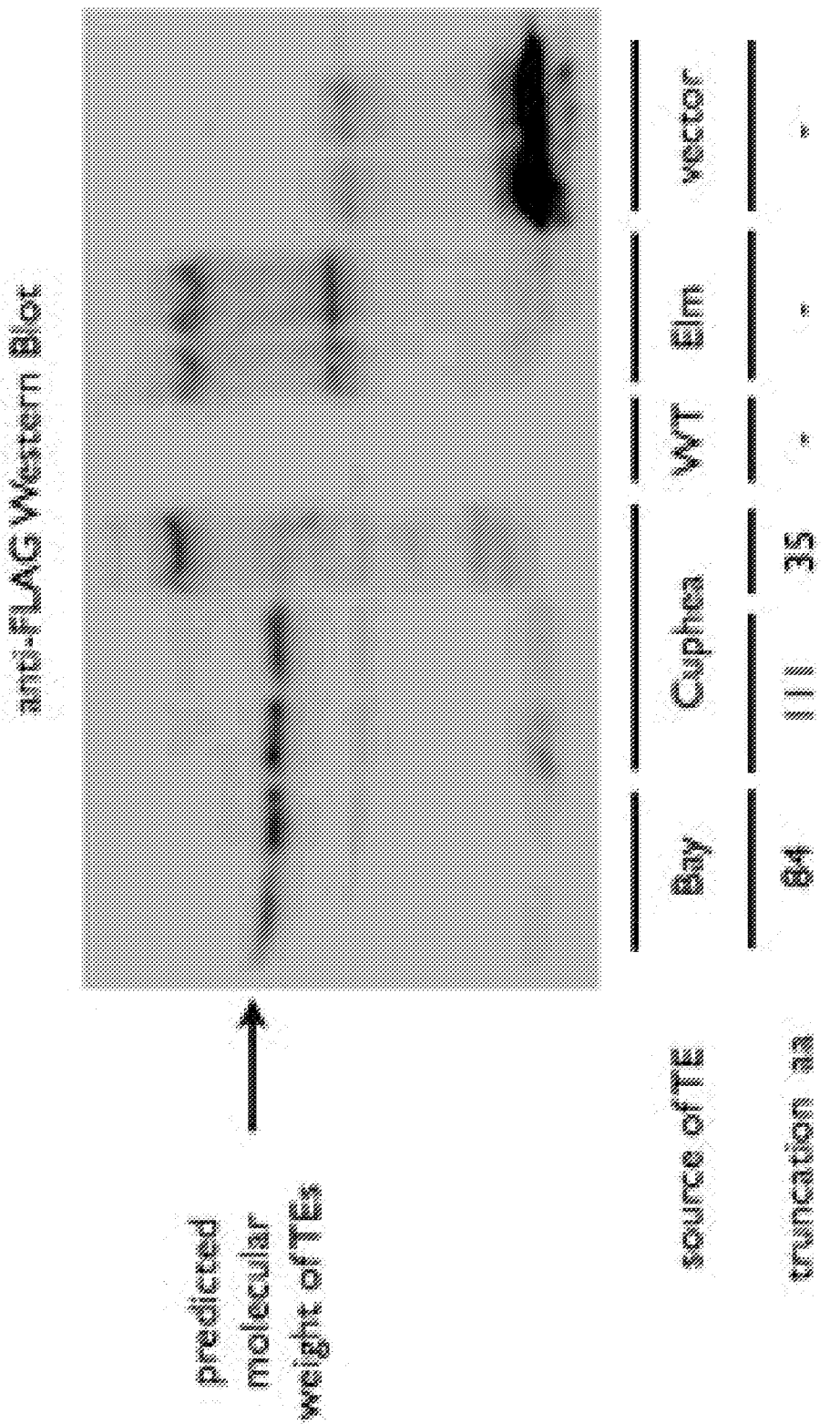
FIG. 1 illustrates a Western blot showing the protein expression levels of several FLAG tagged thioesterases, as discussed in Example 1, below.

In alternative embodiments the invention provides methods and compositions for the production of fatty acids, e.g., renewable fatty acids, from photosynthetic prokaryotic microorganisms, such as Cyanobacteria. In alternative embodiments, engineered or natural strains of these organisms are used to produce saturated or unsaturated, or both saturated and unsaturated fatty acids, with variable chain length specificity, e.g. from between about 8 to 18 carbons, or having a variable chain length specificity of between about 8 to about 18 carbons, or between about 6 to about 20 carbons, or about 6, 7, 8, 9, 10, 11, 12, 13, 14, 15, 16, 17, 18, 19 or 20 or more carbons.

In alternative embodiments, the invention provides methods to extract and analyze various fatty acids, as well as methods to screen strain libraries for fatty acid secretion.

Some embodiments include methods of utilizing photosynthetic microorganisms in the production of fatty acids. In alternative embodiment, any photosynthetic microorganism or combination thereof is used; including any photosynthetic microorganism which can be grouped into one of two classes: green algae and blue green algae (e.g., Cyanobacteria)—both green algae and blue green algae obtain their energy through photosynthesis. Whereas green algae comprise a large group of eukaryotic microorganisms related to plants, blue green algae (Cyanobacteria) are prokaryotes and belong to a single phylum Cyanophyta. In alternative embodiments, any specie of Cyanobacteria is used as a photosynthetic microorganism to practice this invention. However a person of ordinary skill will recognize that the modifications and methods described herein can be applied to chloroplasts of green algae (which evolutionarily originated from Cyanophyta or Cyanobacteria) and blue green algae. Thus, in alternative embodiments, any specie of chloroplast of any green algae can be used to practice this invention.

In alternative embodiments, Cyanobacteria used to practice the invention comprise a wide range of species, all of which fix carbon dioxide, and some which also fix atmospheric nitrogen. In alternative embodiments, Cyanobacterial species are able to grow, and for the invention are grown, in a variety of environments under highly variable salt, pH and temperature conditions. In alternative embodiments, Cyanobacteria used to practice the invention also comprise species cultivated outdoors in open ponds, e.g., species used for neutraceuticals.

In alternative embodiments, Cyanobacteria used to practice the invention belong to one or more of the following genera, including all modifications and methods described herein: *Anabaena* sp., such as *Anabaena* PCC7120, *Aphani*- zomenon sp., *Aphanocapsa* sp., *Aphanothece* sp., *Arthrospira* sp., *Calothrix* sp., *Cylindrospermum* sp., *Dermocarpa* sp., *Eucapsis* sp., *Fischerella* sp., *Geitlerinema* sp., *Gloeocapsa* sp., *Gloeotrichia* sp., *Lyngbya* sp., *Mastigocladus* sp., *Merismopedia* sp., *Microcoleus* sp., *Microcystis* sp., *Nodularia* sp., *Nostoc* sp., *Oscillatoria* sp., *Phormidium* sp., *Plectonema* sp., *Pseudoanabaena* sp., *Schizotrix* sp., *Scytonema* sp., *Spirulina* sp., *Starria* sp., *Symphyonemopsis* sp., *Symploca* sp., *Synechococcus* sp., such as *Synechococcus elongatus* PCC7942, *Synechocystis* sp. and *Tolypothrix* sp.

In alternative embodiments, nitrogen fixing species are used to practice the invention, and these can comprise species of the genera: *Anabaena, Nostoc* and *Nodularia*; unicellular species of the genus: *Synechococcus, Synechocystis* and *Aphanothece*; and filamentous species of the genus: *Lyngbya, Oscillatoria, Phormidium, Pseudoanabaena, Arthrospira* and *Spirulina*.

In addition to genome modifications, methods of the invention also comprise harvesting (isolating) fatty acids from lipids that naturally occur in Cyanobacteria. In alternative embodiments, Cyanobacteria-isolated phospholipid and glycolipids are isolated and/or converted into fatty acids using enzymatic or chemical protocols. In alternative embodiments, Cyanobacteria belonging to the following genus are used to obtain lipids/fatty acids: *Anabaena* sp., *Aphanizomenon* sp., *Aphanocapsa* sp., *Aphanothece* sp., *Arthrospira* sp., *Calothrix* sp., *Cylindrospermum* sp., *Dermocarpa* sp., *Eucapsis* sp., *Fischerella* sp., *Geitlerinema* sp., *Gloeocapsa* sp., *Gloeotrichia* sp., *Lyngbya* sp., *Mastigocladus* sp., *Merismopedia* sp., *Microcoleus* sp., *Microcystis* sp., *Nodularia* sp., *Nostoc* sp., *Oscillatoria* sp., *Phormidium* sp., *Plectonema* sp., *Pseudoanabaena* sp., *Schizotrix* sp., *Scytonema* sp., *Spirulina* sp., *Starria* sp., *Symphyonemopsis* sp., *Symploca* sp., *Synechococcus* sp., *Synechocystis* sp. and *Tolypothrix* sp.

In alternative embodiments, the invention uses any method or media for culturing of photosynthetic microorganisms or modified chloroplast organelles, e.g., for the production of fatty acids. Various methods of culture of photosynthetic microorganisms or modified chloroplast organelles can be employed, including closed or open bioreactors using sunlight or artificial light, using monochromatic or polychromatic light, and using phototrophic or heterotrophic conditions, with or without agitation, in suspension or not, in mono-culture (single species) or in co-culture (two or more species, at least one of which is a photosynthetic microorganism). Any form of culture container or bioreactor can be used to grow, culture, and or harvest photosynthetic prokaryotic microorganisms used to practice the compositions and methods of this invention. For example, in one embodiment, cyanobacteria are genetically engineered to have lower RUBISCO (ribulose-1,5-bisphosphate carboxylase/oxygenase) content in order to grow more efficiently at elevated carbon dioxide levels while recycling industrial carbon dioxide emissions back to products, as described e.g., in U.S. Pat. App. No. 20100081177. In one embodiment, a closed-loop system for growing algae is used, as described e.g., in U.S. Pat. App. No. 20100003717. In one embodiment, methods for culturing blue-green algae as described e.g., in U.S. Pat. App. No. 20050037480, are used. In one embodiment, processes for outdoor thin-layer cultivation of microalgae and blue-green algae and bioreactors for performing these process as described e.g., in U.S. Pat. Nos. 5,541,056, and 5,981,271, are used. In one embodiment, water-insoluble particulates or fibrous supports as described e.g., in U.S. Pat. No. 4,950,601, are used. In alternative embodiments, bioreactor systems and methods as described e.g., in U.S. Pat. Nos. 5,447,866; 5,958, 761 (describing a bioreactor for improved productivity of photosynthetic algae); U.S. Pat. Nos. 6,174,720; 6,326,191; 6,432,698; 6,571,735; 6,673,532; 6,942,799; 7,041,493; 7,176,017; 7,176,024; and 7,682,823, are used. In alternative embodiments, apparatus and methods for cultivating photosynthetic organisms, such as algae, as described e.g., in U.S. Pat. App. Pub. Nos. 20090151240, and 20100034050, are used.

Alternative embodiments include methods of genome modification in photosynthetic microorganisms and chloroplast organelles. For example, delivery of exogenous nucleic acid (e.g. DNA) into photosynthetic cells and organelles can be carried out using several mechanisms, including: bombardment of cells with gold particles coated with nucleic acid (e.g. DNA), conjugation of nucleic acid (e.g. DNA) using a host such as *E. coli*, electroporation of nucleic acid (e.g. DNA), transduction with a virus or natural transformation of nucleic acid (e.g. DNA) into the microorganism. Methods of conjugation and natural transformation are described herein. In addition, modification of the genome can include targeted or random homologous integration into the genome or use of a self-replicating plasmid. Whereas the examples described herein demonstrate natural transformation with homologous integration in the genome, one with ordinary skill in the art will recognize that other genome modifications can be used to produce similar results.

Alternative embodiments include methods for heterologous expression of proteins using an inducible promoter system, e.g. in a blue green algae, any specie of the phylum Cyanophyta, a chloroplast of a green algae or a Cyanobacterium. For example, in alternative embodiments, inducible expression systems and promoters for use with Cyanobacterium as described in U.S. Pat. App. Nos. 20020164706 and 20090104656 can be used.

In some embodiments, vectors comprise nucleic acid (e.g. DNA), fragments having the following functions: lacI repressor, Ptrc promoter, lac operon, gene of interest, rrnB terminator sequence and an antibiotic resistance marker flanked by sequences homologous to the species' genome into which the fragment is to be integrated. In addition to the elements described above, vectors can also contain an origin of replication that allows for replication of the vector. In alternative embodiments, expression of heterologous genes in photosynthetic microorganisms may or may not involve recombination into the genome. In alternative embodiments, expression of heterologous genes does not require an inducible promoter such as Ptrc and can also be achieved with a constitutive promoter. In alternative embodiments, the presence of the rrnB terminator is optional, heterologous protein expression can be achieved with or without a terminator. In alternative embodiments, the presence of an antibiotic marker allows for quick identification of clones carrying the construct, but is not required for heterologous gene expression. In alternative embodiments, both endogenous (from the same species) as well as exogenous (from another species) genes can be expressed containing either native DNA sequence or DNA sequence that has be codon-optimized for an organism of choice. In alternative embodiments, one skilled in the art will recognize that any vector where the nucleic acid fragment to be expressed can be operably linked to a promoter with transcriptional and translational initiation and termination regulatory sequences (that are functional in the host cells) would produce similar results.

In alternative embodiments, the invention uses nucleic acid sequences encoding genes whose protein product encodes a polypeptide, an enzyme, an esterase, a thioesterase and/or an acyl-ACP thioesterase. In alternative embodiments, an acyl-ACP thioesterase includes any sequence of amino acids which demonstrates an ability to catalyze the release of free fatty acids from an acyl-ACP substrate.

In alternative embodiments, the invention uses polypeptides, enzymes, esterases and/or thioesterases in photosynthetic microorganisms or organelles for the production of free fatty acids. In alternative embodiments, the expression of a thioesterase in a photosynthetic microorganism or organelles results in the ability of the microorganism to produce free fatty acids. In alternative embodiments, a variety of fatty acids are produced with expression of different thioesterases. For example, in alternative embodiments, expression of *Umbellularia californica* FatB results in production of high levels of laurate (C12:0) with negligible amounts of other fatty acids. In alternative embodiments, expression of *Cuphea hookeriana* ChFatB2 and *Ulmus americana* UaFatB1 results in production of high levels of octanoate (C8:0 with minor C10:0) and palmitate (C16:0), respectively, as pure fatty acids. In alternative embodiments, expression of oleoyl specific thioesterases from *Carthamus tinctorius* and *Brassica napus* produces palmitate (C16:0) and stearate (C18:0) rather than oleate (C18:1) (as previously demonstrated in plants). The chain length specificity is more tightly controlled in cyanobacteria than previously demonstrated using these genes in *E. coli* with expression of *Ulmus americana* thioesterase leading to production of C8, C10, C16 as well as unsaturated fatty acids in *E. coli*. Moreover, the chain length specificity varies in Cyanobacteria as compared to the observed activities in plants and *E. coli*.

Alternative embodiments include modifications to the coding sequence of a polypeptide, enzyme, esterase and/or thioesterase nucleic acid or gene to allow for their use in photosynthetic microorganisms. For example, in alternative embodiments, full length coding sequences of polypeptides, enzymes, esterases and/or thioesterases (including those of plant origin) are used, and these can be designed to lose (e.g., have deleted) or have otherwise inactivated plastid targeting sequences at the N-terminus of the protein product. Presence of plastid targeting sequences at the N-terminus of the protein product can target the polypeptide, enzyme, esterase and/or thioesterase to the membrane of the cell, likely resulting in its secretion outside the cell's inner membrane. Alternative embodiments can also include endogenous or comprise exogenous or heterologous sequences such as plastid or other (e.g., plant organelle) targeting sequences.

Full length thioesterases are active in plants, but they show negligible activity in photosynthetic microorganisms. The removal of the N-terminal plastic signaling sequence may be desirable for the thioesterases to be active in photosynthetic microorganisms, and this removal is provided in preferred embodiments.

In alternative embodiments, in practicing this invention any gene encoding a polypeptide, enzyme, esterase and/or thioesterase can be used for the production of a free fatty acid. Genes encoding a polypeptide, enzyme, esterase and/or thioesterase can be found using nucleic acid (e.g., DNA) or protein (amino acid) sequence homology. Genes encoding thioesterases of desired specificity can be obtained using nucleic acid (e.g., DNA) or protein (amino acid) sequence homology to the known polypeptide, enzyme, esterase and/or thioesterase of desired specificity.

In alternative embodiments, polypeptide, enzyme, esterase and/or thioesterase enzymes can be "evolved" (e.g., genetically modified) for chain length specificity, degree of unsaturation as well as improved kinetics. For example, thioesterases from microbial sources that show at least 25% sequence homology to plant thioesterases described herein and can be found in the following microorganisms: *Desulfovibrio vulgaris, Spirosoma linguale, Microscilla marina, Clostridium acetobutylicum, Elusimicrobium minutum, Clostridium thermocellum, Clostridium tetani, Anaeromyxobacter dehalogenans, Anaeromyxobacter* sp., *Moorella thermoacetica, Geobacter metallireducens, Carnobacterium* sp., *Clostridium butyricum, Geobacter* sp., *Rhodothermus marinus, Clostridium* sp., *Clostridium botulinum* and *Alkaliphilus oremlandii*.

In one embodiment, pure fatty acid feedstock can be obtained (are produced) through expression of a single thioesterase; in alternative embodiments, fatty acids of various chain lengths can be obtained (are produced) by co-expressing two or more thioesterases. For example, in alternative embodiments, to produce C8-C12 saturated fatty acids, expression of both the *Cuphea hookeriana* and *Umbellularia californica* thioesterases can be used.

Some embodiments include the use of nucleic acid sequences encoding genes whose protein product is a stearoyl-ACP-desaturase (or a protein having a stearoyl-ACP-desaturase activity). In alternative embodiments, stearoyl-ACP-desaturase used to practice the invention include any amino acid sequence (any polypeptide) which demonstrates activity to catalyze the conversion of stearoyl-ACP to oleoyl-ACP. In alternative embodiments, a substrate of stearoyl-ACP desaturase comprising stearoyl-ACP (C18:0) is used; alternatively, as these enzymes also show activity on shorter acyl chains (for example C16:0), and thus can also convert C16:0-ACP to C16:1-ACP, shorter acyl chains (for example C16:0 or less) also can be used to practice the invention.

In alternative embodiments, nucleic acids encoding acyl-ACP-desaturases and β-hydroxydecanoyl dehydrase are used to practice the invention, and methods of the invention can express these enzymes or equivalents thereof. For example, in alternative embodiments, in addition to introducing double bonds at the end of fatty acid biosynthesis using a stearoyl-ACP desaturase, double bonds can also be introduced earlier in fatty acid biosynthesis, resulting in the same end product, C16:1-ACP or C18:1-ACP. For example, microbial fatty acid biosynthesis (excluding cyanobacteria) consists of a branch point at the level of a C10 hydroxy intermediate, which can be converted by β-hydroxydecanoyl dehydrase into two isomers, a trans-2,3 and the cis-3,4 unsaturated C10 intermediates, of which the first gives rise to saturated acyl chains and the second to unsaturated acyl chains at the end of fatty acid biosynthesis. One with ordinary skill in the art will recognize that genes encoding acyl-ACP-desaturases and β-hydroxydecanoyl dehydrase can be found using nucleic acid (e.g., DNA) or protein (e.g., amino acid) sequence homology from other organisms and used as described herein.

In alternative embodiments, an oleoyl- or palmitoleoyl-ACP thioesterase is co-expressed with a stearoyl-ACP-desaturase in practicing the methods and compositions of the invention because Cyanobacteria do not introduce double bonds into the growing acyl chain during fatty acid biosynthesis. Stand-alone expression of a thioesterase in Cyanobacteria can only yield saturated fatty acids as free fatty acids. Thus, in alternative embodiments, if the production of free unsaturated fatty acids is desired, an oleoyl- or palmitoleoyl-ACP thioesterase is co-expressed with a stearoyl-ACP-desaturase.

For example, co-expression of an oleoyl-ACP thioesterase and a stearoyl-ACP-desaturase in *S. elongatus* resulted in production of palmitoleate (C16:1). Whereas expression of stearoyl-ACP-desaturase in heterotrophic bacteria like *E. coli* results in inactive protein due to lack of ferredoxin, this is not a limitation in photosynthetic microorganisms—especially in Cyanobacteria, making Cyanobacteria suitable for the expression of active stearoyl-ACP-desaturase.

In alternative embodiments, fatty acids described herein which are naturally secreted from Cyanobacteria are harvested (e.g., isolated) or exploited for downstream use. In alternative embodiments, efficient secretion of fatty acids is important for several reasons; it reduces intracellular toxicity, reduces feedback inhibition of fatty acid biosynthesis by removing the product outside of the cell and it allows for facile physical separation of the fatty acid product from cell mass. In alternative embodiments, a secretion phenotype is used to practice the invention, and it can be the result of expression of a thioesterase (as wild-type cells also secrete fatty acids, albeit at low levels). Thus one with ordinary skill in the art will recognize that production of fatty acids in photosynthetic microorganisms does not necessarily require secretion of fatty acids and whether the fatty acids are secreted is a function of the host employed.

In alternative embodiments, the invention provides for the expression of endogenous or heterologous acyl-ACP synthase, or alternatively, to decrease or shut down expression of acyl-CoA synthetase, if appropriate. Cyanobacteria do not utilize fatty acids as an energy source due to lack of β-oxidation capacity. Whereas $E.$ $coli$ utilize exogenous fatty acids as an energy source by coupling them to CoA with the help of acyl-CoA synthetase and subsequently breaking them down to acetyl-CoA, Cyanobacteria lack this activity. Instead, Cyanobacteria couple exogenous fatty acids to ACP using acyl-ACP synthase. Those precursors are then gradually incorporated into lipids. Thus whereas acyl-CoA synthetase activity in $E.$ $coli$ directly competes with a thioesterase by committing the acyl chain to a degradation pathway, the acyl-ACP synthetase in Cyanobacteria simply reverses the thioesterase activity. This unique feature of Cyanobacteria allows for standalone expression of a thioesterase in Cyanobacteria resulting in high levels of fatty acid production as described herein.

Some embodiments include methods to extract fatty acids. In alternative embodiments, various methods of fatty acid extraction from aqueous media are utilized to recover free fatty acids. These methods can include solvent extraction, thin layer chromatography, supercritical solvent extraction, distillation, partial pressure distillation and solid phase extraction. In alternative embodiments, solid phase extraction is used; medium chain fatty acids, especially octanoate and decanoate, have short aliphatic chain length making it difficult to efficiently extract from aqueous solvents—thus in some embodiments solid phase extraction is preferred. In alternative embodiments, reverse phase solid phase extraction is used using e.g., hydrophobic resin (C18) to recover medium chain fatty acids with nearly 100% efficiency. One with ordinary skill in the art will recognize that in practicing the invention other hydrophobic resins (e.g., C8) also can be used in solid phase extraction of medium chain fatty acids from aqueous solutions.

Some embodiments include methods for high-throughput screening for fatty acid secretion. Secretion of fatty acids of intermediate chain length C14-C18 (saturated or unsaturated) results in formation of a precipitate on top of the culture. The precipitate consists of salts of fatty acids (e.g., myristate, palmitate and stearate). Some embodiments include methods to collect precipitated fatty acids of intermediate chain length by skimming the surface of a culture.

Methods to analyze free fatty acids are also provided herein. Whereas most fatty acid analyses required conversion of fatty acids to fatty acid methyl esters, analysis of medium chain fatty acids in such a way results in molecules with very high volatility, resulting in large sample loses prior to analysis and inaccurate measurements of yield. Described herein are methods to analyze medium chain fatty acids as free fatty acids. Of special interest are methods to analyze free fatty acids using HP-FFAP™ (Aqilent, Santa Clara, Calif., US) columns coupled to gas chromatography mass spectrometry.

These and many other variations and embodiments of the invention will be apparent to one of skill in the art upon a review of the appended description and examples. The invention will be further described with reference to the following examples; however, it is to be understood that the invention is not limited to such examples.

EXAMPLES

Example 1

Expression of Thioesterases in Cyanobacteria

The full length plant thioesterases (TEs), as well as ACP-desaturase, were synthesized and codon optimized for $S.$ $elongatus$. Genes used in the examples provided herein are shown in Table 1. Accession numbers AAB71731, AAC49001, AAC49269, AAA33020, CAA52069 and AAA74692 are incorporated herein by reference in their entireties.

TABLE 1

| Species | Gene | Accession Number | Short designation | Truncated Residues |
|---------|------|------------------|-------------------|--------------------|
| Ulmus americana | UaFatB1 | AAB71731 | Elm TE | none |
| Umbellularia californica | FatB | AAC49001 | Bay TE | none |
| Umbellularia californica | FatB | AAC49001 | truncBay TE | 1-83 |
| Cuphea hookeriana | ChFatB2 | AAC49269 | Cuphea TE | none |
| Cuphea hookeriana | ChFatB2 | AAC49269 | truncCuphea TE | 1-110 |
| Carthamus tinctorius | Oleoyl-ACP thioesterase | AAA33020 | Safflower TE | none |
| Carthamus tinctorius | Oleoyl-ACP thioesterase | AAA33020 | truncSafflower TE | 1-60 |
| Brassica napus | Oleoyl-ACP thioesterase | CAA52069 | Rapeseed TE | none |
| Brassica napus | Oleoyl-ACP thioesterase | CAA52069 | truncRapeseed TE | 1-48 |
| Ricinus communis | Stearoyl-ACP desaturase | AAA74692 | ACP-desaturase | 1-33 |

Genes were cloned behind an IPTG inducible promoter and integrated into $S.$ $elongatus$ genome using natural DNA transformation of the organism. For protein expression analysis, 3×FLAG peptide was added at the N-terminus. Strains expressing heterologous genes were cultured under constant light conditions with 100 µE fluorescent light, 30° C. and agitation at 150 rpm. Cultures were supplemented with exogenous carbon dioxide once every 24 h. Expression of heterologous proteins was induced with 1 mM IPTG during log-phase growth at OD 730 between 1 to 2. Following a period of induction of greater than (>) 24 hours (h), cells were harvested for protein expression analysis and supernatant was saved for analysis of fatty acid content. An anti-FLAG Western blot in FIG. 1 shows the protein expression levels of several FLAG tagged thioesterases. The arrow indicates the predicted molecular weight of the thioesterases. Both the truncated Cuphea TE (truncated to eliminate amino acid residues 1 to 110) and truncated Bay TE (truncated to eliminate amino acid residues 1 to 83) were expressed showing bands with correct molecular weight.

Example 2

Secretion of Saturated Fatty Acids

Figure 2:
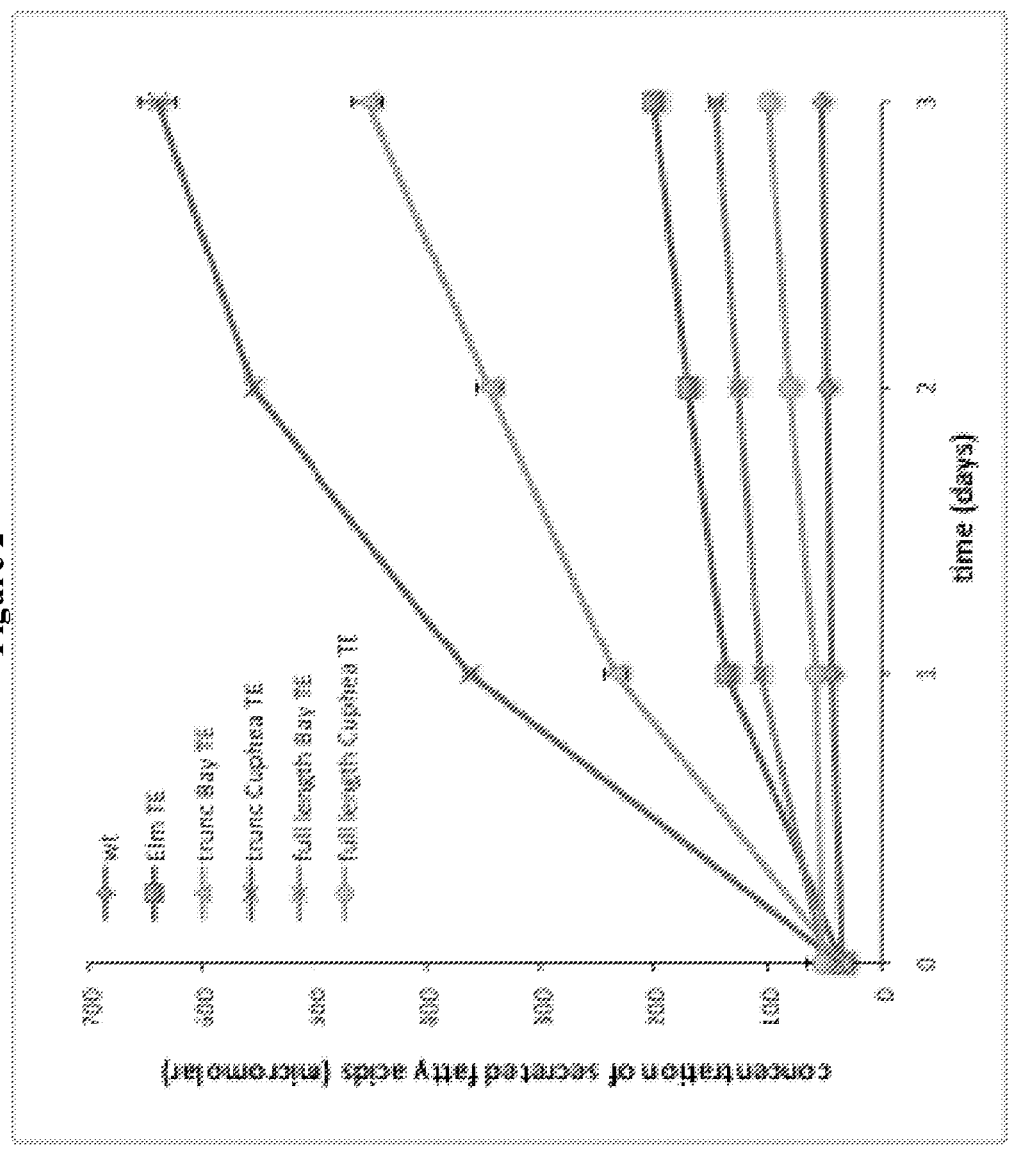
FIG. 2 graphically illustrates data showing the accumulation of fatty acids in the culture medium over time following induction with IPTG, as discussed in Example 2, below.

The activity of the thioesterases was evaluated as a function of fatty acid concentration secreted into the culture medium using a commercially available colorimetric assay. FIG. 2 shows the accumulation of fatty acids in the culture medium over time following induction with IPTG. After 3 days of induction the truncBay TE and truncCuphea TE strains show up to approximately 600 µM total secreted fatty acids, a 10 fold elevation over wild-type levels. Full length thioesterases show much reduced activity with levels of secreted fatty acids only about 2 fold higher than levels in wild-type cells.

Example 3

Secretion of Unsaturated Fatty Acids

Cyanobacteria do not introduce double bonds into the growing acyl chain during fatty acid synthesis. Thus stand-alone expression of a thioesterase in cyanobacteria can only yield saturated fatty acids (as shown in Example 4). Plants are capable of introducing a double bond in the growing acyl chain using a stearoyl-ACP desaturase; however, expression of such a desaturase in heterotrophic bacteria like E. coli results in inactive protein due to lack of ferredoxin, which is not a limitation in cyanobacteria.

Co-expression of an oleoyl-ACP thioesterase and a stearoyl-ACP desaturase in S. elongatus resulted in secretion of fatty acids into the culture medium. The activity of thioesterases was evaluated after 60 h of IPTG induction (Table 2) and measured (as in Example 2). Whereas strains expressing an ACP-desaturase and an inactive thioesterase make only 75 µM total fatty acids, strains expressing an ACP-desaturase and active oleoyl-ACP thioesterases produce about 230-280 µM total fatty acids. Profile of fatty acids is show in Example 4 (Table 4), with highest elevation of C16:1 following expression of truncRapeseed TE and ACP-desaturase.

TABLE 2

| Thioesterase | Desaturase | Fatty acid concentration (µM) |
|---|---|---|
| Inactive truncSafflower TE[a] | ACP-desaturase | 75 |
| truncSafflower TE | ACP-desaturase | 233 |
| truncRapeseed TE | ACP-desaturase | 281 |

[a]A point mutant was obtained that showed no thioesterase activity and was used as a negative control in this experiment. Wild type cells carrying empty plasmid typically secrete 60 µM fatty acids after about 60 h induction with IPTG.

Example 4

Fatty Acid Profile of Strains

To evaluate the identity of the fatty acids produced in the TE-expressing strains, the following procedure was used to isolate the fatty acids from the culture media and analyze the constituent fatty acids using mass spectrometry (MS). The cells were cultured and induced with IPTG as described above. After three days, the cells were spun down and the media fraction containing fatty acids was saved. This fraction was then acidified and bound to C18 solid phase extraction columns. Fatty acids were eluted with dichloromethane and then analyzed by GC/MS. An Agilent (Santa Clara, Calif., US) HP-FFAP™ column was used that allows for facile resolution of free fatty acids. Following resolution of the fatty acids by GC, the fatty acids were fragmented by electron ionization and the resulting ions were detected by MS. The combination of fragmentation pattern as well as matching retention time with commercial standards allowed for identification of fatty acid species produced by the TE-expressing strains.

The composition of fatty acids produced by the strains described above has been characterized and is shown in Tables 3 and 4. Values represent concentration of fatty acids in µM as determined by GC/MS using internal standards. Only saturated fatty acids were detected when a stand alone thioesterase was expressed with highest levels of C8:0 and C10:0 observed after truncCuphea TE expression, C12:0 after truncBay TE expression, C14:0 after Elm TE expression and C16:0 after truncRapeseed TE expression. Unsaturated fatty acid, C16:1, was elevated after expression of truncRapeseed TE and ACP-desaturase.

TABLE 3

| Thioesterase | C8 | C10 | C12 | C14 | C16 | C18 |
|---|---|---|---|---|---|---|
| none | 2.2 ± 0.1 | 2.1 ± 0.4 | nd | 0.6 ± 0.2 | 4.3 ± 0.5 | 9.1 ± 2.0 |
| Elm TE | 6.6 ± 0.2 | 9.2 ± 0.6 | nd | 17.6 ± 1.9 | 66.9 ± 20 | 7.7 ± 0.2 |
| truncBay TE | 2.4 ± 0.1 | 2.8 ± 0.9 | 73.2 ± 2.9 | 6.0 ± 0.4 | 5.1 ± 0.5 | 7.4 ± 0.2 |
| truncCuphea TE | 338 ± 7.0 | 84.4 ± 4.2 | nd | 1.7 ± 1.3 | 18.9 ± 2.8 | 8.0 ± 0.6 |

TABLE 4

| Thioesterase | desaturase | C16:0 | C16:1 | C18:0 | C18:1 |
|---|---|---|---|---|---|
| Inactive truncSafflower TE[a] | ACP-desaturase | 1 | 4 | 6 | 11 |
| truncSafflower TE | ACP-desaturase | 4 | 11 | nd | 4 |
| truncRapeseed TE | ACP-desaturase | 27 | 20 | nd | 3 |
| truncSafflower TE | none | 76 | nd | 34 | nd |
| truncRapeseed TE | none | 91 | 9 | 18 | nd |

[a]A point mutant was obtained that showed no thioesterase activity and was used as a negative control in this experiment. Wild type cells carrying empty plasmid typically secrete 60 µM fatty acids after about 60 h induction with IPTG.

Example 5

Fatty Acid Metabolism in Cyanobacteria

Figure 3:
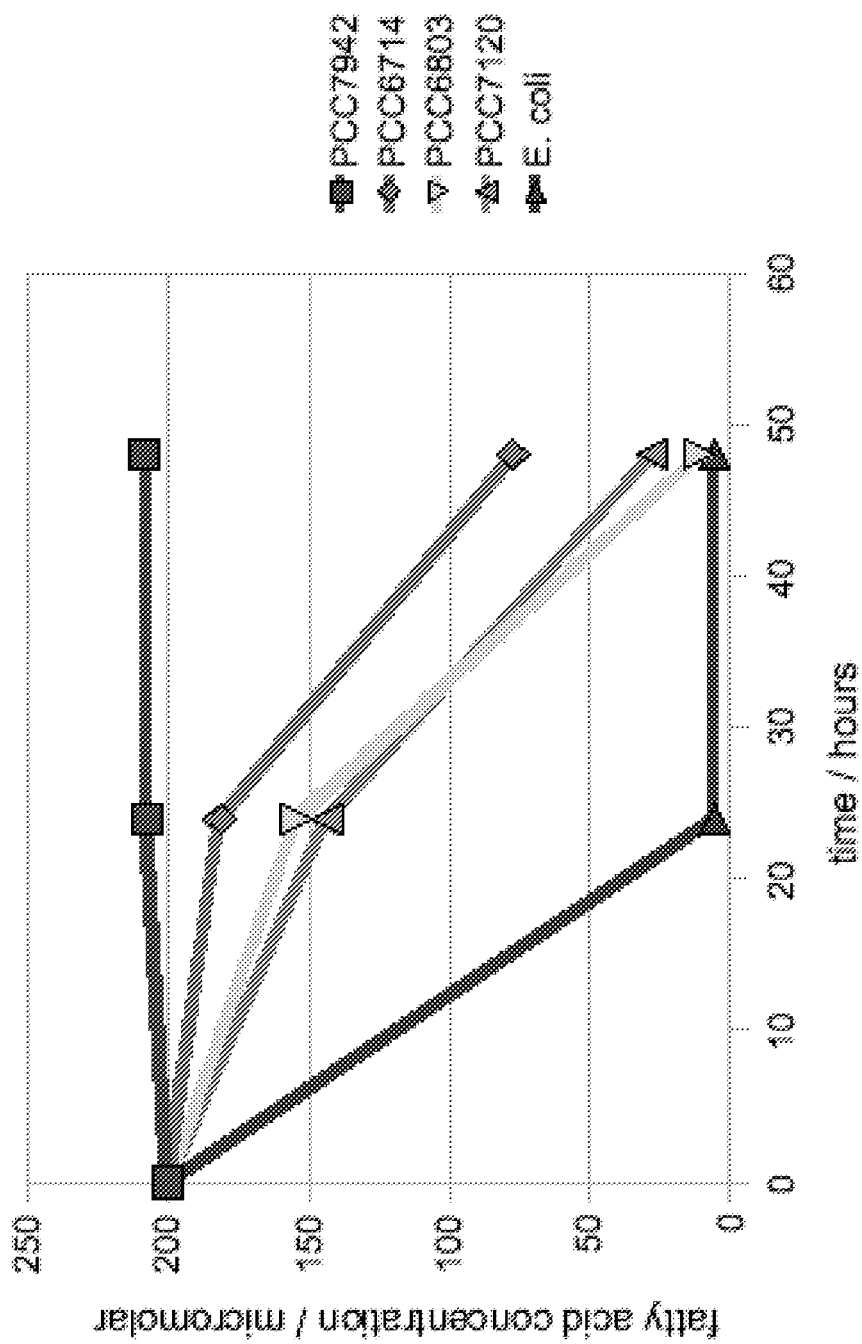
FIG. 3 graphically illustrates data showing the uptake and metabolism of octanoate by *E. coli* and Cyanobacterial cultures, as discussed in Example 5, below.

To compare the ability of cyanobacteria and *E. coli* to metabolize exogenous fatty acids, various strains of cyanobacteria and a strain of *E. coli* were cultured in the presence of octanoate. Octanoate was added to 200 µM to the culture media and its concentration was measured at 0, 24 and 48 hours during growth. Octanoate was chosen due to high solubility in media, allowing for measurement of fatty acid concentrations over time as described in Example 2. All saturated cultures were diluted 1:5. Cyanobacteria were cultured in BG11 media with agitation at 30° C., 100 µE constant light, whereas *E. coli* was cultured in with agitation at 37° C. in LB media. The strains below are PCC7942—*S. elongatus* PCC7942, PCC6714—*Synechocystis* PCC6714, PCC6803—*Synechocystis* PCC6803, PCC7120—*Anabaena* PCC7120 and *E. Coli*—TOP10 (Invitrogen). FIG. 3 clearly shows that whereas octanoate is completely taken up and metabolized by *E. coli* within 24 hours, more than 75% of octanoate remains in the cyanobacterial cultures after 24 hours. Moreover, *S. elongatus* PCC7942 did not take up and metabolize octanoate to any extent during 48 hours of growth—making this organism most suitable for production of fatty acids.

Example 6

Expression Thioesterase in Engineered *Anabaena* and *Synechococcus*

Expression of plant medium chain thioesterases in *Anabaena* results in the secretion of high levels of saturated fatty acids into the culture medium as shown in Table 2, below. Although the same genes were expressed in *Anabaena* and *Synechococcus*, the profile of secreted fatty acids is not the same in both organisms suggesting that the specificity of the thioesterases depends in part on the organism from which they are expressed.

For example, expression of Elm thioesterase in *Synechococcus* results in elevated C14 and C16 secreted fatty acids where as expression in *Anabaena* results in elevated C8 secretion. Similarly Bay thioesterase expressed in *Anabaena* shows low specificity in fatty acids profile.

TABLE 2

Concentration of secretable fatty acids (µM) upon expression of plant medium chain thioesterases in *Anabaena* PCC7120:

| Fatty acid | Bay TE | Cuphea TE | Elm TE |
|---|---|---|---|
| C8  | nd          | 651.2 ± 51.1 | 71.6 ± 4.5 |
| C10 | 5.7 ± 1.2   | 22.5 ± 1.2   | 23.1 ± 3.3 |
| C12 | 25.4 ± 9.0  | nd           | nd         |
| C14 | 25.7 ± 16.5 | nd           | nd         |
| C16 | 21.7 ± 2.2  | 5.5 ± 9.5    | 23.0 ± 1.8 |
| C18 | 43.9 ± 2.3  | 29.4 ± 3.3   | 26.6 ± 0.7 |

Legend for Table 2: Cuphea TE refers to expression of Cuphea ChFatB2 thioesterase, Elm TE refers to expression of Elm UaFatB1 thioesterase, Bay TE refers to expression of Bay FatB thioesterase, nd means not detected. No secreted fatty acids were detected in wild type *Anabaena* cells carrying an empty plasmid. All genes were expressed from a copper inducible promoter.

Figure 4:
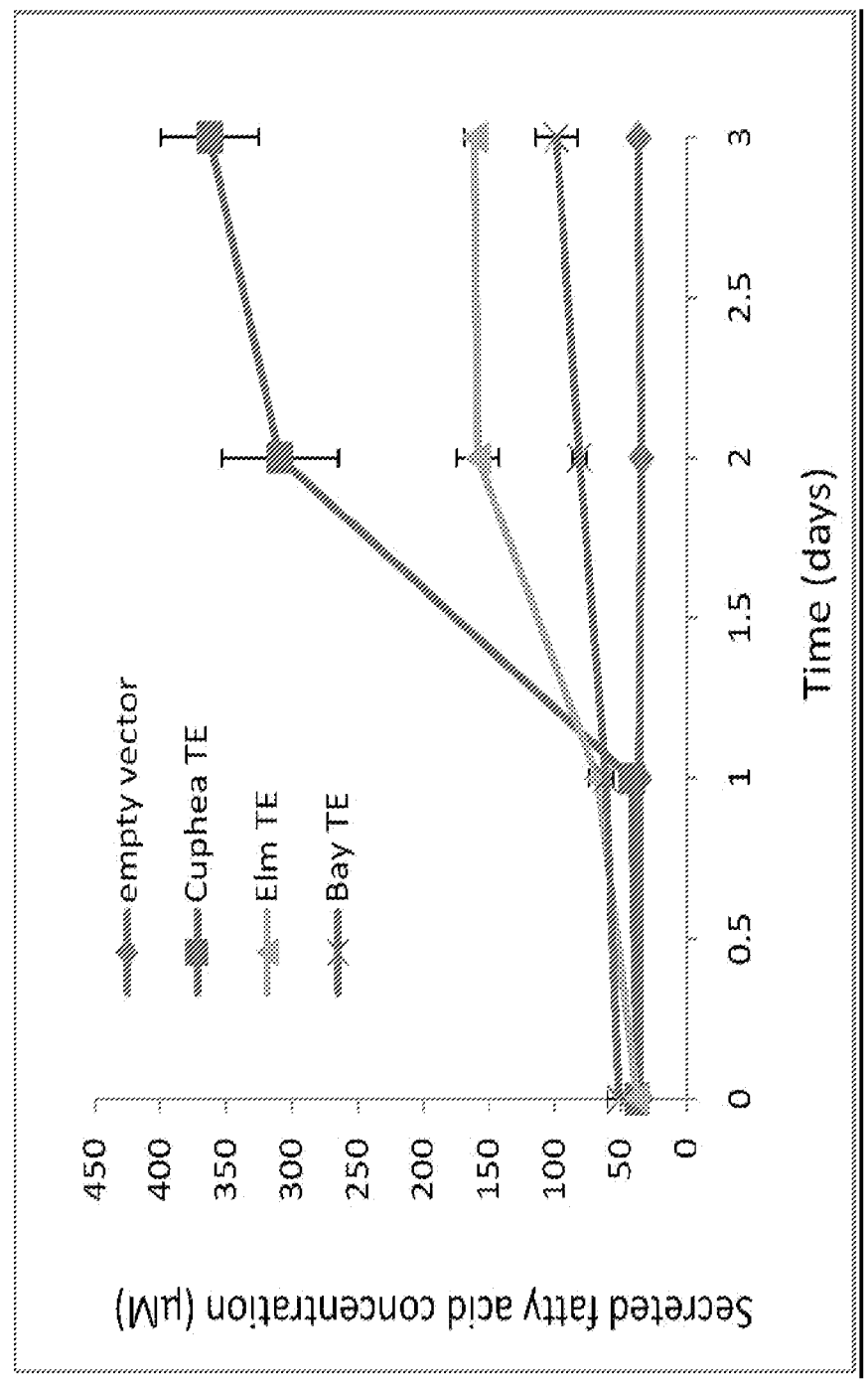
FIG. 4 graphically illustrates data from a study of the secretion of fatty acids from *Anabaena* PCC7120-expressing thioesterase genes, as discussed in Example 6, below.

The activity of thioesterases in *Anabaena* PCC7120 was evaluated as a function of fatty acids concentration secreted into the culture medium over time using a commercially available colorimetric assay, as illustrated in FIG. 4, which illustrate data from study of the secretion of fatty acids from *Anabaena* PCC7120 expressing thioesterase genes.

A number of aspects of the invention have been described. Nevertheless, it will be understood that various modifications may be made without departing from the spirit and scope of the invention. Accordingly, other aspects are within the scope of the following claims.

What is claimed is:

1. A method for producing a monounsaturated fatty acid in a photosynthetic Cyanobacterium comprising:
   (i) providing a photosynthetic Cyanobacterium, wherein the photosynthetic Cyanobacterium is:
      (a) genetically engineered to have a disrupted chromosomal ribulose-1,5-bisphosphate carboxylase/oxygenase (RUBISCO) gene;
      (b) transformed with a nucleic acid comprising a promoter sequence operably linked to a heterologous nucleic acid sequence encoding a stearoyl-acyl carrier protein (ACP)-desaturase polypeptide which produces or catalyzes the synthesis of a monounsaturated fatty acid-ACP in the photosynthetic Cyanobacterium, and
      (c) transformed with a nucleic acid comprising a promoter sequence operably linked to a heterologous nucleic acid sequence encoding an oleoyl- and/or a palmitoleoyl-acyl carrier protein (ACP) thioesterase, wherein the thioesterase hydrolyses ACP from a growing acyl chain to terminate elongation of the acyl chain to form a fatty acid,
   wherein co-expression of the oleoyl- and/or palmitoleoyl-ACP thioesterase with the stearoyl-ACP-desaturase in the photosynthetic Cyanobacterium produces or catalyzes the synthesis of a monounsaturated fatty acid in the photosynthetic Cyanobacterium; and
   (ii) culturing the photosynthetic Cyanobacterium in a culture medium such that the oleoyl- and/or palmitoleoyl-ACP thioesterase is or are co-expressed with the stearoyl-ACP-desaturase, thereby producing the monounsaturated fatty acid.

2. The method of claim 1, wherein the promoter sequence comprises an inducible promoter sequence or a constitutive promoter sequence.

3. The method of claim 1, further comprising
   extracting the monounsaturated fatty acid from the photosynthetic Cyanobacterium and/or the culture medium; or
   analyzing the monounsaturated fatty acid.

4. The method of claim 1, wherein the photosynthetic Cyanobacterium is further transformed with a heterologous nucleic acid sequence encoding a β-hydroxydecanoyl dehydrase.

5. The method of claim 1, wherein the oleoyl- and/or palmitoleoyl-ACP thioesterase and/or the stearoyl-ACP-desaturase lacks a signaling sequence or an N-terminal plastid signaling sequence, or has been engineered to lack a signaling sequence or an N-terminal plastid signaling sequence.

6. The method of claim 1, wherein the photosynthetic Cyanobacterium is further transformed with a plurality of heterologous nucleic acid sequences encoding a plurality of thioesterases or esterases.

7. The method of claim 1, wherein the heterologous nucleic acid further comprises a sequence selected from the group consisting of: a lad repressor binding site, a Ptrc promoter, a lac operon, a gene of interest, an rrnB terminator sequence, an antibiotic resistance marker, and an origin of replication.

8. The method of claim 1, wherein the photosynthetic Cyanobacterium is selected from the group consisting of *Anabaena* sp., *Aphanizomenon* sp., *Aphanocapsa* sp., *Aphanothece* sp., *Arthrospira* sp., *Calothrix* sp., *Cylindrospermum* sp., *Dermocarpa* sp., *Eucapsis* sp., *Fischerella* sp., *Geitlerinema* sp., *Gloeocapsa* sp., *Gloeotrichia* sp., *Lyngbya* sp., *Mastigocladus* sp., *Merismopedia* sp., *Microcoleus* sp., *Microcystis* sp., *Nodularia* sp., *Nostoc* sp., *Oscillatoria* sp., *Phormidium* sp., *Plectonema* sp., *Pseudoanabaena* sp., *Schizotrix* sp., *Scytonema* sp., *Spirulina* sp., *Starria* sp., *Symphyonemopsis* sp., *Symploca* sp., *Synechococcus* sp., *Synechocystis* sp. and *Tolypothrix* sp.

9. The method of claim 1, wherein the method further comprises extracting and/or isolating the monounsaturated fatty acid from the photosynthetic Cyanobacterium or the culture medium.

10. The method of claim 9, further comprising analyzing the extracted or isolated monounsaturated fatty acid comprising use of
one or more columns or solid phase extraction columns, wherein the one or more columns are optionally coupled to a gas chromatography mass spectrometer.

11. The method of claim 9, further comprising quantifying the amount of fatty acid produced.

12. The method of claim 3, wherein the culture medium comprises an aqueous culture medium.

13. The method of claim 9, wherein the extracting or isolating comprises skimming the surface of the culture medium.

14. The method of claim 1, wherein the disrupted chromosomal ribulose-1,5-bisphosphate carboxylase/oxygenase (RUBISCO) gene of the photosynthetic Cyanobacterium results in a lower ribulose-1,5-bisphosphate carboxylase/oxygenase content.

15. The method of claim 1, wherein the nucleic acid is contained in an expression system, virus or a plasmid.

16. The method of claim 15, wherein the expression system or plasmid is designed for targeted or random homologous integration into the Cyanobacterium genome, or the plasmid is a self-replicating plasmid.

17. The method of claim 1, wherein the monounsaturated fatty acid has a length of between 6 to 20 carbons.

18. The method of claim 17, wherein the monounsaturated fatty acid has a length of between 8 to 18 carbons.

19. The method of claim 1, wherein the monounsaturated fatty acid comprises a C16:1 or a C18:1 monounsaturated fatty acid.

* * * * *